(12) United States Patent
Hall

(10) Patent No.: US 6,644,103 B1
(45) Date of Patent: Nov. 11, 2003

(54) METHOD AND APPARATUS FOR DETECTING A DRY/WET STATE OF A THERMISTOR BEAD

(75) Inventor: Robbie William Hall, Charlotte, VT (US)

(73) Assignee: Simmonds Precision Products, Inc., Charlotte, NC (US)

(*) Notice: Subject to any disclaimer, the term of this patent is extended or adjusted under 35 U.S.C. 154(b) by 0 days.

(21) Appl. No.: 10/313,483

(22) Filed: Dec. 5, 2002

Related U.S. Application Data (63) Continuation-in-part of application No. 10/279,668, filed on Oct. 24, 2002.

(51) Int. Cl.[7] ............................................. G01N 25/56
(52) U.S. Cl. .......................... 73/73; 73/77; 340/604; 324/664
(58) Field of Search ............................. 340/604; 73/77, 73/73; 324/664, 665

(56) References Cited

U.S. PATENT DOCUMENTS

| | | | | |
|---|---|---|---|---|
| 4,872,340 A | * | 10/1989 | de Yong | 73/335.02 |
| 4,901,061 A | * | 2/1990 | Twerdochlib | 340/604 |
| 5,534,708 A | * | 7/1996 | Ellinger et al. | 250/577 |
| 5,880,480 A | * | 3/1999 | Ellinger et al. | 250/577 |
| 6,208,254 B1 | * | 3/2001 | McQueen et al. | 340/603 |

* cited by examiner

Primary Examiner—Hezron Williams
Assistant Examiner—Rodney Frank
(74) Attorney, Agent, or Firm—David R. Percio; Calfee, Halter & Griswold (57) ABSTRACT

A method of detecting a dry/wet state of a thermistor bead comprises the steps of: generating a current waveform that transitions between first and second current levels; conducting the current waveform through the thermistor bead; measuring a voltage waveform across the thermistor bead in response to the current waveform; measuring a slope of the voltage waveform in response to the first and second current levels and generating a first signal indicative of the measured slope; differentiating the voltage waveform to produce a voltage pulse representative of a transition of the voltage waveform from one voltage potential to another and generating a second signal indicative of the polarity of the voltage pulse; and detecting the dry/wet state of the thermistor bead based on the first and second signals. Apparatus for embodying this detection method is also disclosed.

31 Claims, 5 Drawing Sheets

FIGURE 2.

(BACKGROUND)

METHOD AND APPARATUS FOR DETECTING A DRY/WET STATE OF A THERMISTOR BEAD

This application is a continuation-in-part of the U.S. patent application Ser. No. 10/279,668, entitled "Method and Apparatus For Detecting A Dry/Wet State Of A Thermistor Bead", filed Oct. 24, 2002 and assigned to the same assignee as the instant application.

BACKGROUND OF THE INVENTION

The present invention is directed to the detection of dry/wet states of a thermistor bead, in general, and more particularly, to a method and apparatus for detecting a dry/wet state of a thermistor bead based on a difference in voltage across the thermistor bead in response to a difference in current conducted therethrough and on thermistor bead state transition.

Figure 1:
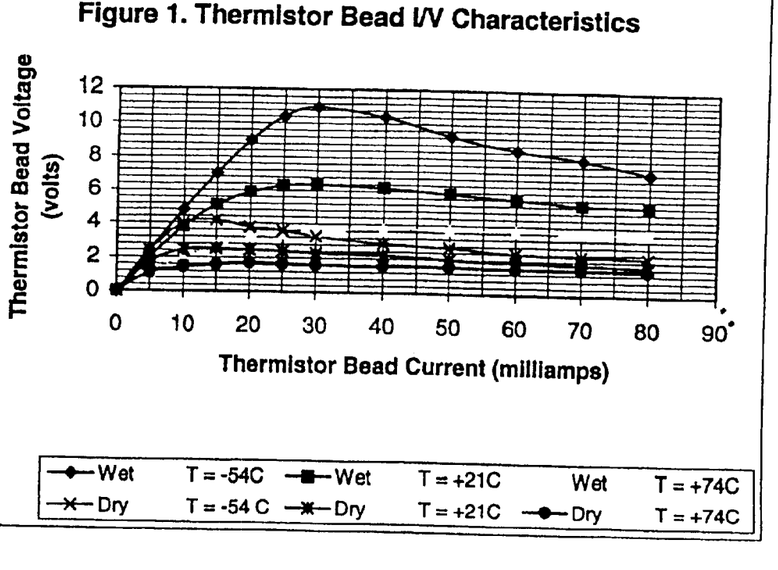
FIG. 1 is a graph depicting dry and wet current vs. voltage characteristics of a typical thermistor bead at various temperatures.

Sensing liquid level in a container, like fuel in an aircraft fuel tank, for example, has been performed using resistive bead type thermistors which have an inverse temperature coefficient. When current is conducted through a thermistor bead in air, i.e. a dry state, the bead increases in temperature and exhibits a low resistance to the current. In contrast, when the thermistor bead is submersed in a liquid, like jet fuel, for example, the bead is cooled and its resistance to current conducted therethrough is increased. Current vs. Voltage (I/V) characteristics of a typical thermistor bead at various temperatures is shown in the graph of FIG. 1. It is readily observable from the graph of FIG. 1 that the voltage across the thermistor becomes a viable measurement for detecting a wet vs. dry (wet/dry) state of the thermistor bead as the current conducted therethrough becomes greater than 45 milliamps. For example, by passing a constant current through a thermistor bead and lowering the bead from the top of the container, it may be determined at what level in the container the thermistor bead becomes submersed into the liquid by detecting the wet/dry state thereof based on the voltage across the thermistor bead.

Figure 2:
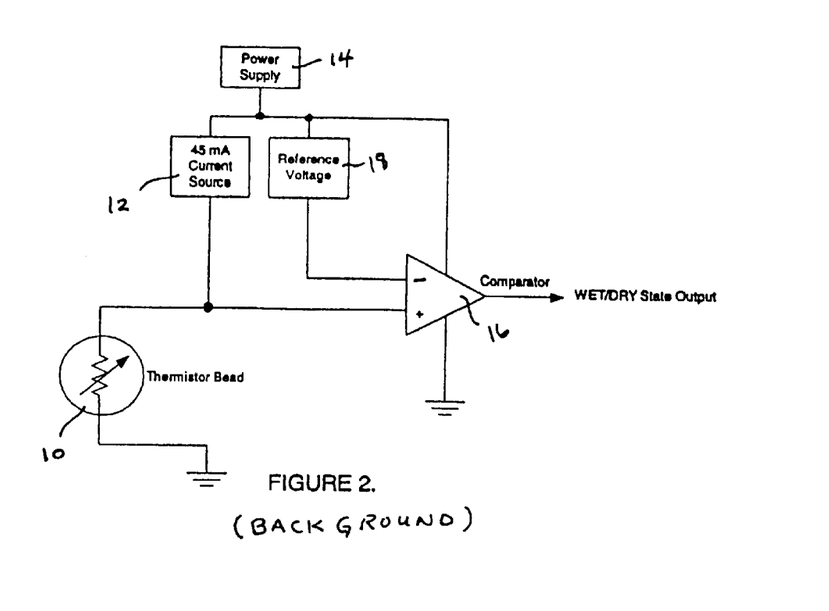
FIG. 2 is a block diagram circuit schematic of interface circuitry for detecting the dry/wet state of a thermistor bead based on a known method.

Known interface circuitry which uses the above described method of detecting the dry/wet state of a thermistor bead is shown in the block diagram schematic of FIG. 2. Referring to FIG. 2, a thermistor bead 10 is coupled between a constant current source 12 and a common or ground return. The constant current source 12 is powered by a power supply and is operative to conduct current through the thermistor bead 10. The voltage across the thermistor bead 10 is sensed by one input of a comparator circuit 16 which is also powered by the supply 14 and common return. A reference voltage is generated by a circuit 18 which is powered by the supply 14. The comparator circuit 16 compares the reference voltage which is coupled to another input thereof with the thermistor bead voltage. When the thermistor bead voltage exceeds the reference voltage, a wet bead state is effected at the output of the comparator 16 and when the thermistor bead voltage is less than the reference voltage, a dry bead state is effected at the output of the comparator 16.

As noted above, to insure proper performance of the thermistor bead and detection circuitry using the above described method, the bead 10 should be biased with a constant current equal to or greater than 45 milliamps where voltage levels across the bead are dry/wet distinct for all practical temperature environments (see the graphs of FIG. 1, for example). For level sensing of combustible liquids in a container with a thermistor bead, the bias current level of 45 milliamps may not be considered safe, and thus unacceptable. For example, the FAA has deemed this bias current level unacceptable in terms of the maximum allowable current that may enter an aircraft fuel tank. Only currents less than 30 milliamps with justification have been deemed acceptable for aircraft fuel tanks. Accordingly, a thermistor bead may not be an acceptable level measurement sensor for combustible liquids in all cases using interface circuitry implementing the above described traditional method.

SUMMARY OF THE INVENTION

In accordance with one aspect of the present invention, a method of detecting a dry/wet state of a thermistor bead comprises the steps of: generating a current waveform that transitions between first and second current levels; conducting the current waveform through the thermistor bead; measuring a difference in voltage across the thermistor bead in response to the first and second current levels; and detecting the dry/wet state of the thermistor bead based on the measured difference in voltage.

In accordance with another aspect of the present invention, apparatus for detecting a dry/wet state of a thermistor bead comprises: a first circuit coupled to the thermistor bead for generating a current waveform that transitions between first and second current levels and for conducting the current waveform through the thermistor bead; a second circuit coupled to the thermistor bead for measuring a difference in voltage across the thermistor bead in response to the first and second current levels; and a third circuit coupled to the second circuit for detecting the dry/wet state of the thermistor bead based on the measured difference in voltage.

In accordance with a further aspect of the present invention, a method of detecting a transient dry/wet state of a thermistor bead comprises the steps of: conducting a current waveform through the thermistor bead; measuring a voltage waveform across the thermistor bead in response to the current waveform; differentiating the voltage waveform to produce a voltage pulse representative of a transition of the voltage waveform from one voltage potential to another; and detecting the transient dry/wet state of the thermistor bead based on the voltage pulse.

In accordance with yet another aspect of the present invention, apparatus for detecting a transient dry/wet state of a thermistor bead comprises: a first circuit coupled to the thermistor bead for conducting a current waveform therethrough; a second circuit coupled to the thermistor bead for measuring a voltage waveform across the thermistor bead in response to the current waveform and differentiating the voltage waveform to produce a voltage pulse representative of a transition of the voltage waveform from one voltage potential to another; and a third circuit coupled to the second circuit for detecting the transient dry/wet state of the thermistor bead based on the voltage pulse.

In accordance with yet another aspect of the present invention, a method of detecting a dry/wet state of a thermistor bead comprises the steps of: generating a current waveform that transitions between first and second current levels; conducting the current waveform through the thermistor bead; measuring a voltage waveform across the thermistor bead in response to the current waveform; measuring a slope of the voltage waveform in response to the first and second current levels and generating a first signal indicative of the measured slope; differentiating the voltage waveform to produce a voltage pulse representative of a transition of the voltage waveform from one voltage potential to another and generating a second signal indicative of the polarity of the voltage pulse; and detecting the dry/wet state of the thermistor bead based on the first and second signals.

In accordance with yet another aspect of the present invention, apparatus for detecting a dry/wet state of a thermistor bead comprises: a circuit coupled to the thermistor bead for generating a current waveform that transitions between first and second current levels and conducting the current waveform through the thermistor bead; a circuit coupled to the thermistor bead for measuring a voltage across the thermistor bead in response to the current waveform and generating a voltage waveform signal representative thereof; a first detector circuit, coupled to the voltage measuring circuit, for determining a slope of the voltage waveform signal in response to the first and second current levels and generating a first signal indicative of the determined slope; a second detector circuit, coupled to the voltage measuring circuit, for differentiating the voltage waveform signal to produce a voltage pulse representative of a transition of the voltage waveform signal from one voltage potential to another and generating a second signal indicative of the polarity of the voltage pulse; and     a logic circuit coupled to the first and second detector circuits for detecting the dry/wet state of the thermistor bead based on the first and second signals generated thereby.

BRIEF DESCRIPTION OF THE DRAWINGS

FIGS. 7A–7H are time graphs suitable for use in describing the operation of the alternate embodiment of FIG. 5.

DETAILED DESCRIPTION OF THE INVENTION

The method and apparatus of the present invention detects the dry/wet state of a thermistor bead for liquid level measurement, but is capable of performing the dry/wet state detection thereof using bias currents substantially less than forty-five milliamps. This method and apparatus may even operate with bias currents less than thirty milliamps for thermistor bead application to measurement of fuel level in an aircraft fuel tank which is considered within the FAA acceptable current levels. As shown in FIG. 1, for all temperature conditions, the current vs. voltage (I/V) characteristics of a thermistor bead at bias currents of less than thirty milliamps (30 ma), and more particularly between fifteen milliamps (15 ma) and twenty-five milliamps (25 ma), for example, the I/V slope characteristics of a dry bead are either less than the I/V slope characteristics of a wet bead or are negative. Thus, the dry/wet state of the thermistor bead for fuel level application in an aircraft fuel tank may be detected based on a voltage slope determination in response to two different bias currents that are both less than thirty milliamps, and thus acceptable from a safety perspective.

Figure 3:
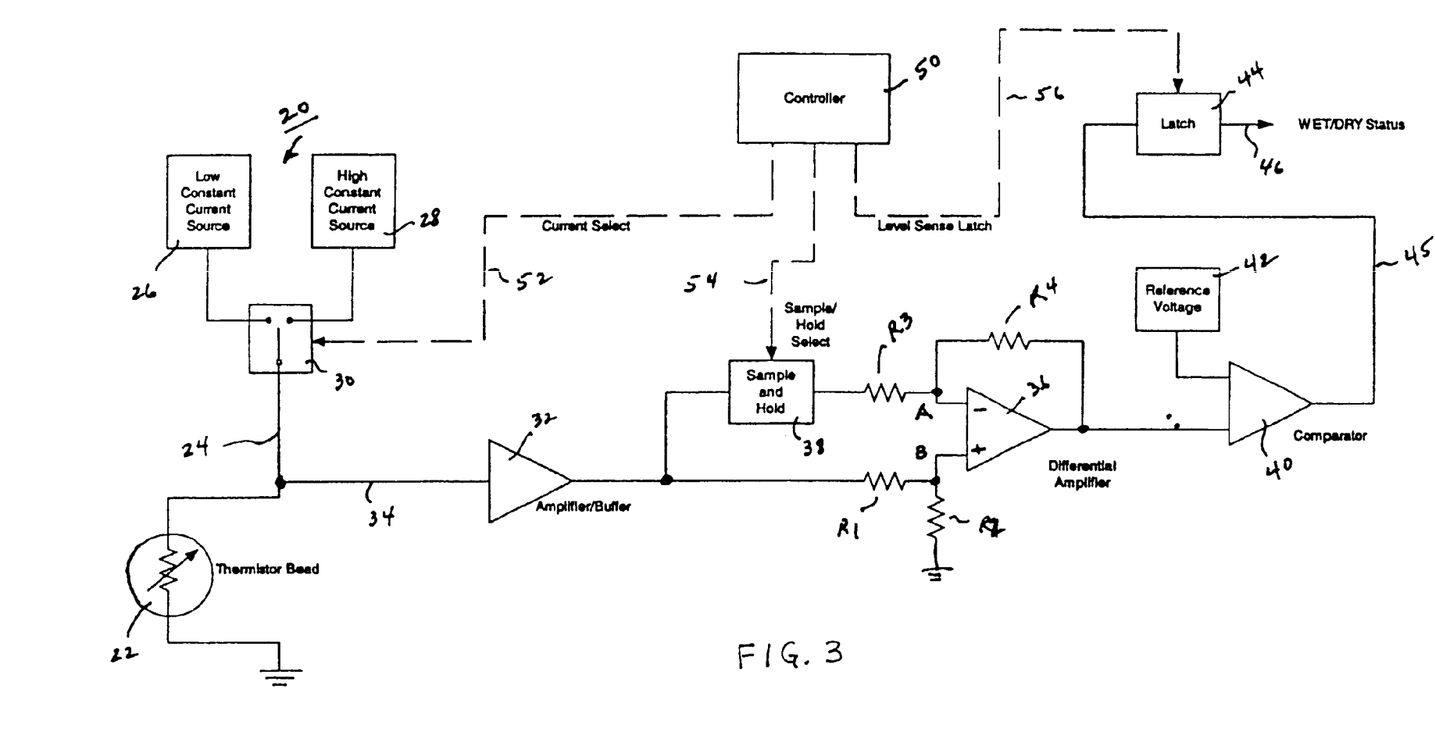
FIG. 3 is a block diagram circuit schematic of apparatus for detecting the dry/wet state of a thermistor bead suitable for embodying the broad principles of the present invention.

A block diagram schematic of apparatus for detecting the dry/wet state of a thermistor bead suitable for embodying the principles of the present invention is shown in FIG. 3. Referring to FIG. 3, a constant current source 20 is coupled to a thermistor bead 22 over a signal line 24. The source 20 is operative to conduct current through the thermistor bead selectively between a first or low current level, like on the order of fifteen milliamps, for example, and a second or high current level, like on the order of twenty-five milliamps, for example. In the present embodiment, the constant current source 20 includes a first or low constant current source 26 for generating current at the first current level, a second constant current source 28 for generating current at the second current level, and a switch 30 for coupling selectively the first and second constant current sources to the thermistor bead 22 over signal 24 for conducting the selected current through the thermistor bead 22 to a common potential. While two constant current sources are used in the present embodiment for the constant current source 20, it is understood that a single constant current source which is selectively controlled to generate either the first current level or second current level may be used just as well without deviating from the broad principles of the present invention.

The voltage developed across the thermistor bead 22 in response to the selected current level may be amplified and buffered by an amplifier circuit 32 which is coupled to the thermistor bead 22 by a signal line 34, for example. An output of the amplifier circuit 32 is coupled to a non-inverting (+) or B input of a differential amplifier circuit 36 via a resistor divider network comprising resistors R1 and R2 coupled in series between amplifier 32 and the common potential. Also coupled to the output of amplifier 32 is a sample-and-hold circuit 38, the output of which being coupled to an inverting (−) or A input of the differential amplifier 36 through a resistor R3. Another resistor R4 is coupled between the output and A input of the amplifier 36. The ratio of resistor values R4 to R3 sets the closed loop gain of the differential amplifier 36.

Still referring to FIG. 3, the output of amplifier 36 is coupled to one input of a comparator circuit 40. A reference voltage generator circuit generates a reference voltage signal which is coupled to another input of comparator circuit 40. An output of comparator 40 may be coupled over a signal line 45 to a latch circuit 44 which provides a signal indicative of the dry/wet state of the thermistor bead 22 over an output signal line 46. In the present embodiment, a controller circuit 50 is coupled to the constant current source 20 via switch 30, the sample-and-hold circuit 38, and the latch circuit 44 over signal lines 52, 54 and 56, respectively, for the time sequence control of the operations thereof as will become more evident from the description provided herein below in connection with the time graphs of FIGS. 4A–4I.

Referring to FIG. 3 and the time graphs pf FIGS. 4A–4I, at time to, controller 50 is operative to control the constant current circuit 20 to conduct current at the first or low current level through the thermistor bead 22 for a period of time, like until time $t_1$, for example. This is accomplished, in the present embodiment, by governing the state of one control signal to switch circuit 30 over signal line 52 in a high state, and another control signal to switch 30 over signal line 52 in a low state as shown by the time graphs of FIGS. 4B and 4A, respectively. During this period from $t_0$ to $t_1$, the voltage across the thermistor bead 22, which is monitored by amplifier/buffer 32, is passed to inputs B and A of the differential amplifier 36 directly from amplifier 32 and through the sample-and-hold circuit 38 as shown by the time graphs of FIGS. 4E and 4D, respectively. The time period $t_0$–$t_1$ is made long enough to permit the voltage across the bead 22 to stabilize substantially in response to the low current level being conducted therethrough.

Figure 4A:
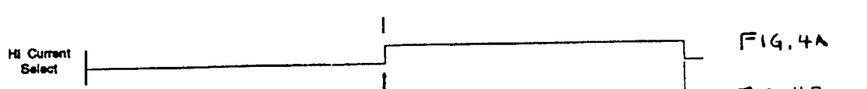
FIGS. 4A–4I are time graphs suitable for use in describing the operation of the embodiment of FIG. 3.
Figures 4B, 4C:
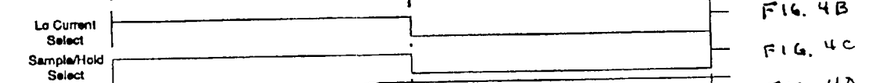

At or around time $t_1$, controller 50 is operative to control the constant current circuit 20 to conduct current at the second or high current level through the thermistor bead 22 for a period of time, like until time $t_3$, for example. This is accomplished, in the present embodiment, by governing the state of the other control signal to switch circuit 30 over signal line 52 in a high state, and the one control signal to switch 30 over signal line 52 in a low state as shown by the time graphs of FIGS. 4A and 4B, respectively. Also, at or around time $t_1$, the controller 50 is operative to control sample-and-hold circuit 38 via signal line 54 as shown in FIG. 4C to capture the bead voltage and hold it for the duration from $t_1$ to $t_3$, for example, as shown in the time graph of FIG. 4D. Thus, the voltage signal at input A of the differential amplifier 36 remains substantially constant at the stabilized voltage of bead 22 in response to the low current level.

Figures 4D, 4E:
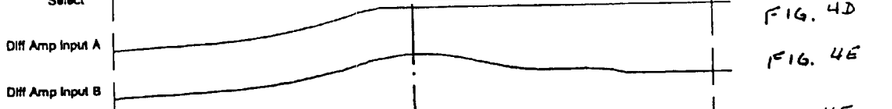

During this period from $t_1$ to around $t_3$, the voltage across the thermistor bead 22 is passed to input B of the differential amplifier 36 directly from amplifier 32, but not passed through the sample-and-hold circuit 38 as shown by the time graphs of FIGS. 4E and 4D, respectively. The time period $t_1$ to $t_3$ is made long enough to permit the voltage across the bead 22 to stabilize substantially in response to the high current level being conducted therethrough as shown by the graph of FIG. 4E. Also, during the period from $t_1$ to $t_3$, the differential amplifier circuit 36 generates a signal indicative of the difference in voltage across the thermistor bead 22 in response to the low and high current levels, or essentially the slope of the voltage characteristic curve of the thermistor bead 22, which is shown by the solid line in the time graph of FIG. 4F.

Figures 4F, 4G:
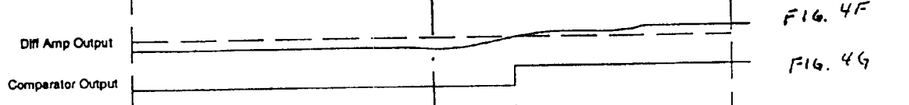
Figures 4H, 4I:
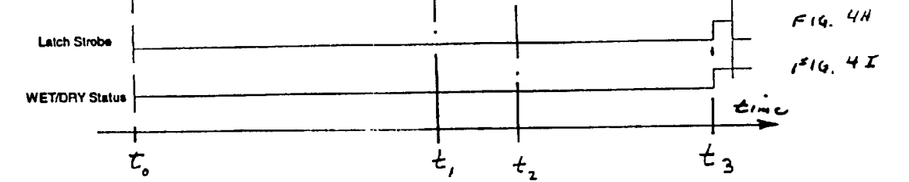

Comparator 40 compares the bead voltage difference or slope signal from amplifier 36 to a reference signal (see dashed line in FIG. 4F) and generates a signal indicative of the comparison results as exemplified in the time graph of FIG. 4G. The reference signal may be set between the slopes of the thermistor characteristic curves indicative of a wet state and the thermistor characteristic curves indicative of a dry state for all operating temperatures (see FIG. 1). Thus, when the slope signal from amplifier 36 exceeds the reference voltage, comparator circuit 40 may generate an output signal in a high state indicative of a wet bead state as shown by the time graph of FIG. 4G at time $t_2$, for example. Of course, if the slope signal from amplifier 36 does not exceed the reference voltage during the time $t_1$ to $t_3$, the output signal of comparator circuit 40 may remain in a low state indicative of a dry bead state.

In the present embodiment, the controller 50 waits until the voltage across the bead 22 is substantially stabilized in response to the high current level before it controls the latch circuit 44 via signal line 56 to capture the comparison results of comparator 40. Accordingly, at or around time $t_3$, controller 50 issues a pulse over signal line 56 to latch 44 (see time graph of FIG. 4H) to control the capture of the comparison result. Thus, after time $t_3$, the output of latch circuit 44 is indicative of the dry/wet state of the thermistor bead 22. The controller 50 may comprise circuits of many different configurations to issue the control signals over lines 52, 54 and 56 in a time sequence as exemplified by the time graphs of 4A–4C and 4H. For example, the controller 50 may be comprised of a counter which is driven to count through a predetermined count by a clock signal and decoders for issuing the control signals at predetermined counts. Controller 50 may also be embodied with a programmed read only memory which outputs the four control signals shown in FIGS. 4A–4C and 4H as governed by the counter which may be coupled to the address inputs thereof. The clock frequency and length of the counter will be determined by the response times of the thermistor bead to the low and high current levels. In any event, the controller 50 may be configured to repeat the time sequence of time graphs 4A–4I for detecting the dry/wet states of the thermistor bead periodically or at predetermined time intervals.

While the present embodiment utilizes a controller for controlling the time sequencing of operations of the various circuits of the detection circuitry, it is understood that such circuits may alternatively operate autonomously without the need of a central control unit. For example, the constant current source 20 may be operative to alternately select the low current level and high current level for conduction through the thermistor bead for predetermined stabilization time periods. In addition, the sample-and-hold circuit 38 may determine when the voltage across the bead 22 has stabilized, and capture and hold the voltage at the output thereof until the next voltage has stabilized, for example. Still further, the latch circuit 44 may monitor the voltage difference signal output from circuit 36 and not capture the comparison result until after the voltage difference signal has stabilized, for example.

In addition, while the present embodiment sequences the low current level and then the high current level through the thermistor bead for determining the slope of the I/V characteristics thereof as a measure of its dry/wet state, it is understood that the sequence could be reversed and the downstream detection circuitry modified to accommodate the change in polarity of the voltage difference or slope signal as a result of the reversal. Such a modification is also considered clearly within the broad principles of the present invention.

In an alternate embodiment for detecting the dry/wet state of the thermistor bead, a transient state detector circuit for detecting the bead's state transitions from wet to dry and dry to wet is added to the I/V slope detector circuit which was described hereabove in connection with the embodiment of FIG. 3. This alternate embodiment is shown, by way of example, in the block diagram schematic of FIG. 5. Reference numerals of circuit elements and interconnections which were described for the embodiment of FIG. 3 will remain the same for the embodiment of FIG. 5. In this alternate embodiment, the buffered bead voltage signal output from the buffer amplifier 32 will not only be input to the IV slope detector circuit 60 as described for the embodiment of FIG. 3, but will also be input to a transient state detector 62 which will be described in greater detail in connection with the embodiment of FIG. 8. In addition, the outputs 46 and 64 of the I/V slope detector and transient state detector circuits, respectively, are input to a selection logic circuit 66 which combines the two signals to determine the dry/wet state of the thermistor bead 22 and generate a signal indicative thereof over signal line 68.

Figure 5:
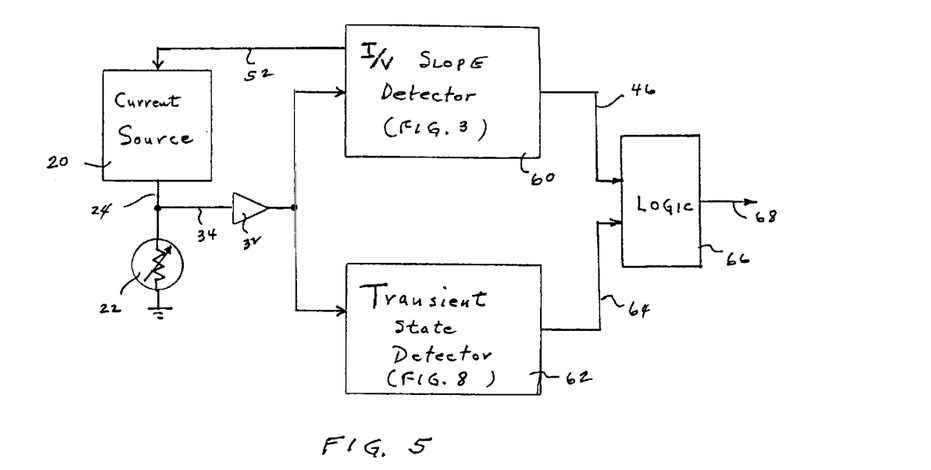
FIG. 5 is a block diagram schematic of an alternate embodiment of the present invention.

Because the input stage of the transient state detector circuit 62 comprises a differentiator circuit as will become more evident from the description thereof herein below, high frequency components on the input bead voltage signal should be avoided. Accordingly, the current source 20 of the embodiment of FIG. 3 will be modified in this alternate embodiment to accommodate the input differentiator circuit stage of the detector 62. A suitable embodiment of a modified current source for use in the alternate embodiment of FIG. 5 is shown in the block diagram schematic of FIG. 6.

Figure 6:
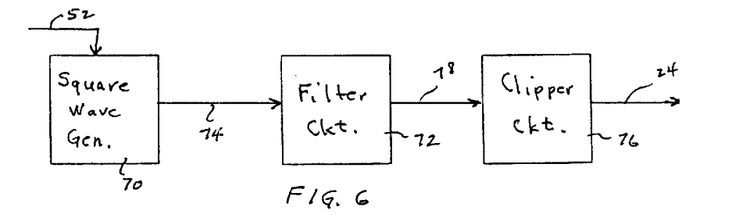
FIG. 6 is a block diagram schematic of a time varying current source suitable for use in the alternate embodiment of FIG. 5.

Referring to FIG. 6, a square waveform generator 70 which may be activated by a control signal from controller 50 over line 52 generates a square wave current signal that transitions between the low and high currents periodically. Both high and low current levels may be below 30 ma. In addition, the frequency of the square wave may be substantially less than one hertz (1 Hz) to provide the thermistor bead substantial time to stabilize at each low and high current interval. The square waveform current signal is coupled to a filter circuit 72 over a signal line 74. The filter circuit 72 may be a low pass circuit designed to remove substantially all of the harmonic frequencies from the current waveform leaving only the fundamental or sinusoidal current waveform which is passed to a clipper circuit 76 over a signal line 78. The clipper circuit 76 is designed to remove the low and high peak current levels of the sinusoidal current waveform to render a flattened or squashed sinusoidal waveform which appears as a trapezoidal like waveform (see FIG. 7A). That is, the resulting waveform from the clipper circuit 76 keeps the low current level substantially constant for about half the period and then, slowly transitions to the high current level which is also kept substantially constant for the next half period and then, slowly transitions back to the low current, and the cycle is repeated. This resulting current waveform is conducted to the thermistor bead 22 over line 24. Accordingly, the voltage across the bead 22 in response to the trapezoidal current waveform will not include high frequency components, and thus is suitable as an input to the differentiator circuit stage of detector 62 via buffer amplifier 32.

Figures 7A, 7H:
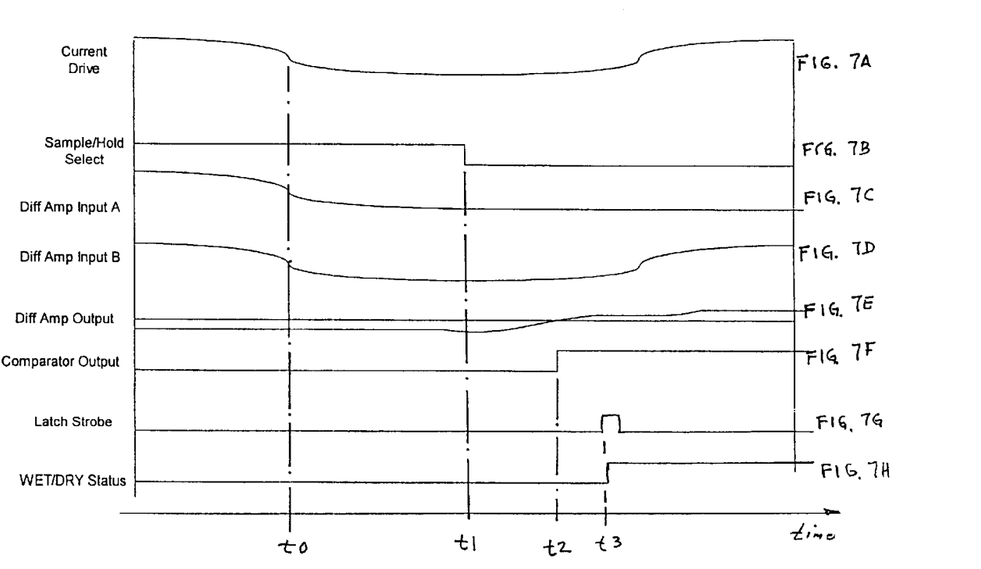

The operation of the I/V slope detector circuit 60 remains substantially the same as described for the embodiment of FIG. 3 except that the transitions between the low and high current levels are not abrupt and discontinuous, but rather smooth and continuous as shown by the waveform in FIG. 7A. The waveforms 7A–7H may be used to describe the operation of the detector circuit 60. The current waveform is transitioned to the low level at t0 and is kept low through the time interval from t0–t1 until the voltage across the bead 22 is stabilized as shown by the waveforms 7C and 7D which are the voltages at the inputs A and B of the differential amplifier 36. At or around t1, the voltage across the bead 22 in response to the low current has stabilized and the sample-and-hold circuit 38 is controlled to capture and hold it (see FIG. 7B). After t1, the current waveform (see FIG. 7A) transitions to the high level and during this time interval the voltage at input B (see FIG. 7D) follows the voltage across bead 22 while the voltage at input A remains fixed at the captured voltage level (see FIG. 7C). Accordingly, the resulting voltage signal (see FIG. 7E) output from the differential amplifier 36 represents the difference between the captured voltage at input A (low current level response) and the voltage at input B (high current level response) or the slope of the I/V characteristics curve. Should this slope voltage exceed the reference voltage, the output of comparator 40 changes to a high state as shown at time t2 which is indicative of a positive slope or wet state. If not, the comparator remains in a low state which is indicative of a dry state. Once the voltage across the bead 22 in response to the high current level has stabilized, like at time t3, for example, the output of the comparator 40 is captured in the latch 44 and output over signal line 46 to the logic circuit 66 (see FIGS. 7G and 7H). The sequence is then repeated for each period of the squashed current sine wave.

Figure 9:
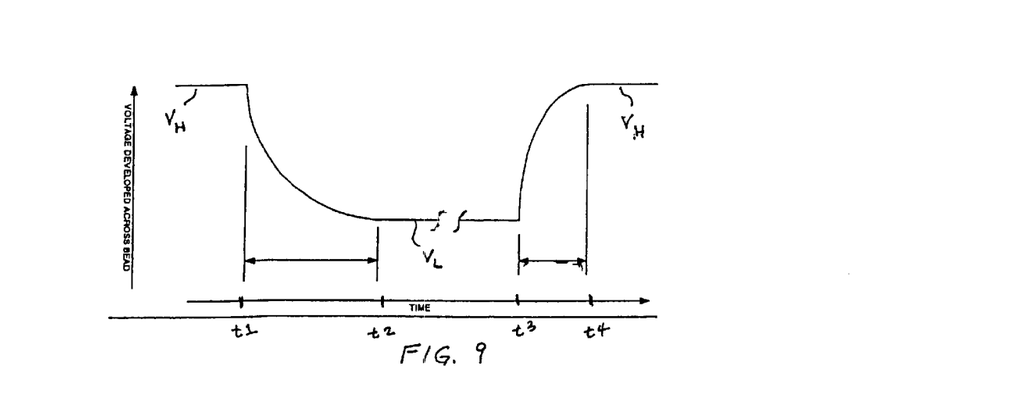
FIG. 9 is an exemplary time graph suitable for illustrating voltage waveform transitions for wet-to-dry and dry-to-wet transient sates of a typical thermistor bead.

Now, referring back to FIG. 5, the transient state detector 62 is operative to determine when the thermistor bead 22 changes from a wet-to-dry state or from a dry-to-wet state and preferably, to do so as the state transition occurs. The detector 62 renders the determination by monitoring the transient voltage response of the thermistor bead. For example, in the exemplary time graph of FIG. 9, when the bead transitions in state from wet-to-dry, the average voltage across the bead in response to the currents conducted therethrough decays from a first voltage potential $V_H$ at time t1 to a lower second voltage potential $V_L$ at time t2. Typically, this transition takes on the order of three to six seconds. Also, as shown in FIG. 9, when the bead transitions in state from dry-to-wet, the average voltage across the bead in response to the currents conducted therethrough rises from the second voltage potential $V_L$ at time t3 to the higher first voltage potential $V_H$ at time t4. For a typical bead, the dry-to-wet transition takes on the order of one-half second.

Figure 8:
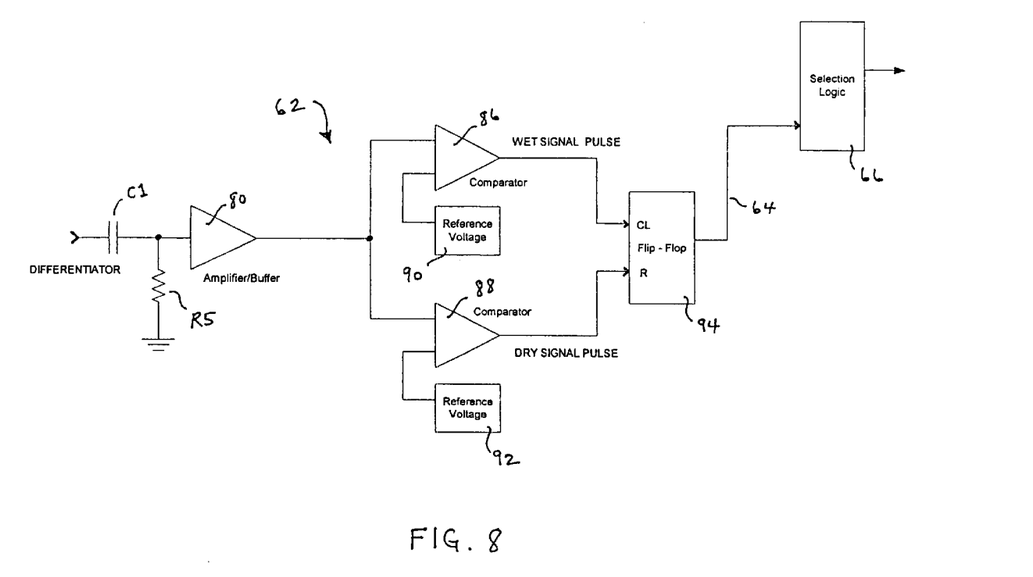
FIG. 8 is a circuit schematic of a transient state detector suitable for use in the alternate embodiment of FIG. 5.

A suitable embodiment for the transient state detector 62 is shown by the circuit diagram of FIG. 8. Referring to FIG. 8, the output of the buffer amplifier 32 which is a voltage representative of the bead voltage is coupled to a differentiator circuit comprising a series capacitor C1 connecting the output of amplifier 32 to another buffer amplifier 80 and a resistor R5 coupling the amplifier 80 side of C1 to ground or common potential. The combination of C1 and R5 forms a cut-off or corner frequency for the differentiator circuit. Preferably, the values of C1 and R5 are chosen such that the corner frequency of the differentiator circuit will pass the wet/dry state transients of the bead, but filter substantially the frequency of the resultant voltage across the bead in response to the current signal supplied thereto.

Figure 10:
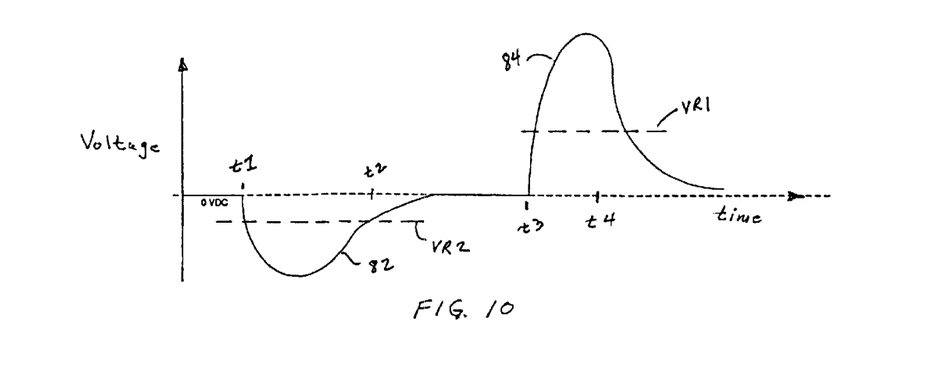
FIG. 10 is an exemplary time graph suitable for illustrating pulse waveform responses to the differentiation of the voltage waveform transitions of FIG. 9.

Accordingly, the output of the amplifier 80 generates a voltage pulse during a state transition of the bead. For example, as shown in the time graph of FIG. 10, as the bead voltage decays from t1 to t2 (FIG. 9) during a wet-to-dry transition, the differentiator circuit produces a negative voltage pulse signal 82 which is representative of the time derivative or slope of the voltage decay. Likewise, as the bead voltage rises from t3 to t4 (FIG. 9) during a dry-to-wet transition, the differentiator circuit produces a positive voltage pulse signal 84 which is representative of the time derivative or slope of the voltage rise.

Also, in the transient state detector 62, the output of amplifier 80 is coupled to an input of each of two comparator circuits 86 and 88. The other input of comparator 86 is coupled to a positive reference voltage VR1 generated by a reference voltage generator 90 and the other input of comparator 88 is coupled to a negative reference voltage VR2 generated by another voltage reference generator 92. Thus, comparator 86 produces a positive pulse indicative of a transition resulting in a wet state and comparator 88 produces a positive pulse indicative of a transition resulting in a dry state. The outputs of both comparators are coupled to a flip-flop circuit 94 which generates an output over signal 64. In the present embodiment, the output of comparator 86 is coupled to a clock input of the flip-flop 94 and the output of comparator 88 is coupled to a reset input thereof. The flip-flop 94 responds to the pulsed output of comparator 86 by setting its output signal high over signal line 64 indicative of a state transition resulting in a wet state and responds to the pulsed output of comparator 88 by resetting its output signal low over signal line 64 indicative of a state transition resulting in a dry state.

As described in connection with the embodiment of FIG. 5 above, the outputs of the detectors 60 and 62 are input to a selection logic circuit 66 which combines the two signals to determine the ultimate dry/wet state of the bead. Note that upon power turn-on, the transient state detector 62 can not determine the bead's dry/wet state because of the input differentiator circuit stage. Thus, the logic circuit 66 determines the initial power-on dry/wet state of the bead from the I/V slope detector 60. Thereafter, the logic circuit 66 may determine the dry/wet state of the thermistor bead immediately from the output of the transient state detector 62 which determines the resulting state of a bead transition at the time of state transition, and uses the bead state determination of the I/V slope detector 60 which requires time for stabilization for confirmation.

Accordingly, while the present invention has been described herein above in connection with one or more possible embodiments, it is understood that there is no intention to limit the invention in any way, shape or form by such embodiments. Rather, the present invention should be construed in breadth and broad scope in accordance with the recitation of the claims appended hereto.

What is claimed is:

1. Method of detecting a dry/wet state of a thermistor bead comprising the steps of:

generating a current waveform that transitions between first and second current levels;

conducting said current waveform through said thermistor bead;

measuring a difference in voltage across said thermistor bead in response to said first and second current levels; and detecting said dry/wet state of said thermistor bead based on said measured difference in voltage.

2. The method of claim 1 wherein the first and second current levels are both generated at less than thirty milliamps.

3. The method of claim 1 wherein the first current level is generated on the order of fifteen milliamps and the second current level is generated on the order of twenty-five milliamps.

4. The method of claim 1 wherein the current waveform is generated as a periodic waveform.

5. The method of claim 1 wherein the current waveform is generated to transition continuously between first and second current levels.

6. The method of claim 1 wherein the step of generating the current waveform includes the steps of:

maintaining current substantially at the first level to be conducted through the thermistor bead for a period of time to permit the voltage across the thermistor bead in response thereto to stabilize substantially; and then, maintaining current at the second level to be conducted through the thermistor bead for a period of time to permit the voltage across the thermistor bead in response thereto to stabilize substantially.

7. The method of claim 6 wherein the step of measuring includes the steps of:

capturing the substantially stabilized voltage value across the thermistor bead in response to the first current level; and determining the difference between the captured voltage value and the substantially stabilized voltage value across the thermistor bead in response to the second current level.

8. The method of claim 7 wherein the step of detecting includes the steps of:

comparing the determined voltage value difference with a reference voltage value;

capturing the comparison result at a time after the voltage across the thermistor bead in response to the second current level has stabilized substantially; and using the captured comparison result to detect the dry/wet state of the thermistor bead.

9. The method of claim 1 wherein the step of detecting includes the steps of:

comparing the measured voltage difference with a reference voltage value; and using the results of said comparison to detect the dry/wet state of the thermistor bead.

10. The method of claim 1 wherein the steps of conducting, measuring and detecting are repeated at predetermined time intervals to detect the dry/wet state of the thermistor bead at each said time interval.

11. Apparatus for detecting a dry/wet state of a thermistor bead comprising:

a first circuit coupled to said thermistor bead for generating a current waveform that transitions between first and second current levels and for conducting said current waveform through said thermistor bead;

a second circuit coupled to said thermistor bead for measuring a difference in voltage across said thermistor bead in response to said first and second current levels; and a third circuit coupled to said second circuit for detecting said dry/wet state of said thermistor bead based on said measured difference in voltage.

12. The apparatus of claim 11 wherein the first circuit includes a time varying current source for generating current at the first level for a period of time to permit the voltage across the thermistor bead in response thereto to stabilize substantially, and then, for generating current at the second level for a period of time to permit the voltage across the thermistor bead in response thereto to stabilize substantially.

13. The apparatus of claim 12 wherein the first circuit includes a circuit for controlling the transition between the first and second current levels to be continuous.

14. The apparatus of claim 12 wherein the first circuit comprises:

a circuit for generating a square waveform current signal;

a filter circuit for receiving and filtering the square waveform current signal to generate a filtered current waveform signal substantially absent harmonic frequency components; and a clipper circuit for receiving and clipping peaks of the filtered current waveform to generate a current waveform that transitions continuously between the first and second current levels.

15. The apparatus of claim 12 wherein the second circuit includes: a circuit coupled to the thermistor bead for capturing the substantially stabilized voltage value across the thermistor bead in response to the first current level; and a circuit coupled to the capturing circuit and the thermistor bead for determining the difference between the captured voltage value and the substantially stabilized voltage value across the thermistor bead in response to the second current level.

16. The apparatus of claim 15 wherein the third circuit includes: a comparator circuit coupled to the voltage difference determining circuit for comparing the determined voltage value difference with a reference voltage value; and a latch circuit coupled to the comparator circuit for capturing an output signal of the comparator circuit at a time after the voltage across the thermistor bead in response to the second current level has stabilized substantially, said captured output signal being indicative of the dry/wet state of the thermistor bead.

17. The apparatus of claim 11 including a controller coupled to the second and third circuits for controlling the operations thereof in a predetermined time sequence.

18. Method of detecting a transient dry/wet state of a thermistor bead comprising the steps of:

conducting a current waveform through said thermistor bead;

measuring a voltage waveform across said thermistor bead in response to said current waveform;

differentiating the voltage waveform to produce a voltage pulse representative of a transition of the voltage waveform from one voltage potential to another; and detecting said transient dry/wet state of said thermistor bead based on said voltage pulse.

19. The method of claim 18 including the step of determining one of a dry-to-wet transient state and a wet-to-dry transient state from the voltage pulse.

20. The method of claim 19 wherein the one transient state is determined based on a polarity of the voltage pulse.

21. The method of claim 19 wherein the step of determining includes; comparing the amplitude of the voltage pulse with two reference voltages of different polarities; and in response to said comparison, generating a signal in a first state indicative of a wet-to-dry transition and in a second state indicative of a dry-to-wet transition.

22. Apparatus for detecting a transient dry/wet state of a thermistor bead comprising:

a first circuit coupled to said thermistor bead for conducting a current waveform therethrough;

a second circuit coupled to said thermistor bead for measuring a voltage waveform across said thermistor bead in response to said current waveform and differentiating the voltage waveform to produce a voltage pulse representative of a transition of the voltage waveform from one voltage potential to another; and a third circuit coupled to said second circuit for detecting said transient dry/wet state of said thermistor bead based on said voltage pulse.

23. The apparatus of claim 22 wherein the third circuit includes a circuit for determining one of a dry-to-wet transient state and a wet-to-dry transient state from a polarity of the voltage pulse.

24. The method of claim 22 wherein the third circuit includes a circuit for comparing an amplitude of the voltage pulse with a first reference voltage of a positive polarity and generating a first signal when said amplitude exceeds the first reference voltage and for comparing said amplitude of the voltage pulse with a second reference voltage of a negative polarity and generating a second signal when said amplitude drops below the second reference voltage; and a circuit for generating a signal in a first state indicative of a dry-to-wet bead transition in response to said first signal, and in a second state indicative of a wet-to-dry bead transition in response to said second signal.

25. Method of detecting a dry/wet state of a thermistor bead comprising the steps of:

generating a current waveform that transitions between first and second current levels;

conducting said current waveform through said thermistor bead;

measuring a voltage waveform across said thermistor bead in response to said current waveform;

measuring a slope of said voltage waveform in response to said first and second current levels and generating a first signal indicative of said measured slope;

differentiating said voltage waveform to produce a voltage pulse representative of a transition of said voltage waveform from one voltage potential to another and generating a second signal indicative of the polarity of said voltage pulse; and detecting said dry/wet state of said thermistor bead based on said first and second signals.

26. The method of claim 25 wherein the step of measuring a slope includes generating a voltage signal representative of the measured slope; and generating the first signal in a first state when the voltage slope signal is above a reference voltage and in a second state when the voltage slope signal is below the reference voltage.

27. The method of claim 25 wherein the second signal is generated in a first state when the voltage pulse exceeds a reference voltage of a positive polarity and in a second state when the voltage pulse drops below a reference voltage of a negative polarity.

28. Apparatus for detecting a dry/wet state of a thermistor bead comprising:

a circuit coupled to said thermistor bead for generating a current waveform that transitions between first and second current levels and conducting said current waveform through said thermistor bead;

a circuit coupled to said thermistor bead for measuring a voltage across said thermistor bead in response to said current waveform and generating a voltage waveform signal representative thereof;

a first detector circuit, coupled to said voltage measuring circuit, for determining a slope of said voltage waveform signal in response to said first and second current levels and generating a first signal indicative of said-determined slope;

a second detector circuit, coupled to said voltage measuring circuit, for differentiating the voltage waveform signal to produce a voltage pulse representative of a transition of the voltage waveform signal from one voltage potential to another and generating a second signal indicative of the polarity of said voltage pulse; and a logic circuit coupled to said first and second detector circuits for detecting said dry/wet state of said thermistor bead based on said first and second signals generated thereby.

29. The apparatus of claim 28 wherein the first detector circuit is operative to generate a voltage slope signal representative of the determined slope, and to generate the first signal in a first state when said voltage slope signal is above a reference voltage and in a second state when said voltage slope signal is below the reference voltage.

30. The apparatus of claim 28 wherein the second detector circuit is operative to generate the second signal in a first state when the voltage pulse is above a reference voltage of a positive polarity and in a second state when the voltage pulse is below a reference voltage of a negative polarity.

31. The apparatus of claim 28 wherein the logic circuit is operative to select the first signal as indicative of the dry/wet state of said thermistor bead upon powering up the apparatus.

* * * * *